(12) United States Patent
Heidenreich et al.

(10) Patent No.: US 9,469,737 B2
(45) Date of Patent: Oct. 18, 2016

(54) ROBUST POLYMERIC MEMBRANE

(71) Applicant: Pall Corporation, Port Washington, NY (US)

(72) Inventors: Erik M. Heidenreich, Pensacola, FL (US); Xuemei Liang, Pensacola, FL (US); Binbing Han, Pensacola, FL (US)

(73) Assignee: Pall Corporation, Port Washington, NY (US)

( * ) Notice: Subject to any disclaimer, the term of this patent is extended or adjusted under 35 U.S.C. 154(b) by 28 days.

(21) Appl. No.: 14/464,201

(22) Filed: Aug. 20, 2014

(65) Prior Publication Data

US 2016/0053064 A1   Feb. 25, 2016

(51) Int. Cl.
| | |
|---|---|
| C08J 9/00 | (2006.01) |
| B01D 39/00 | (2006.01) |
| B01D 39/16 | (2006.01) |
| C07K 1/34 | (2006.01) |
| B01D 67/00 | (2006.01) |
| B01D 71/68 | (2006.01) |
| B01D 71/76 | (2006.01) |

(52) U.S. Cl.
CPC ............. C08J 9/00 (2013.01); B01D 39/1692 (2013.01); B01D 67/0011 (2013.01); B01D 71/68 (2013.01); B01D 71/76 (2013.01); C07K 1/34 (2013.01); B01D 2323/02 (2013.01); C08J 2335/02 (2013.01)

(58) Field of Classification Search
None
See application file for complete search history.

(56) References Cited

U.S. PATENT DOCUMENTS

| | | |
|---|---|---|
| 4,618,533 A | 10/1986 | Steuck |
| 4,943,374 A | 7/1990 | Heininger et al. |
| 5,178,765 A | 1/1993 | Hu et al. |
| 5,282,971 A | 2/1994 | Degen et al. |
| 6,039,872 A | 3/2000 | Wu et al. |
| 6,071,406 A | 6/2000 | Tsou |
| 6,083,393 A | 7/2000 | Wu et al. |
| 6,193,077 B1 | 2/2001 | Witham et al. |
| 6,495,043 B1 | 12/2002 | Heijnen |
| 2003/0198825 A1 | 10/2003 | Mayes et al. |
| 2009/0023623 A1 | 1/2009 | Yamamoto et al. |
| 2009/0176052 A1 | 7/2009 | Childs et al. |
| 2011/0253621 A1* | 10/2011 | Kim .............. B01D 65/08 210/500.39 |
| 2014/0083931 A1 | 3/2014 | Chang et al. |

FOREIGN PATENT DOCUMENTS

| | | |
|---|---|---|
| JP | 2009-185118 A | 8/2009 |
| WO | WO 98/08595 A2 | 3/1998 |
| WO | WO 2004/073843 A1 | 9/2004 |

OTHER PUBLICATIONS

Intellectual Property Office of Singapore, Search Report in Singapore counterpart application No. 10201506167Y, mailed Dec. 10, 2015.

* cited by examiner

*Primary Examiner* — Kara Boyle
(74) *Attorney, Agent, or Firm* — Jeremy Jay

(57) ABSTRACT

Hydrophilic porous membranes comprising a random copolymer of:
(a) 2-hydroxyethyl methacrylate of formula (I):

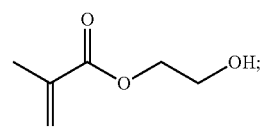

(b) an ethylene glycol dimethacrylate of formula (II):

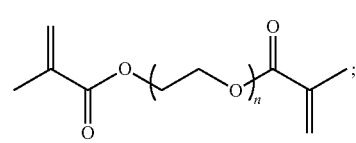

and
(c) 1,1,1-trimethylolpropane trimethacrylate of formula (III):

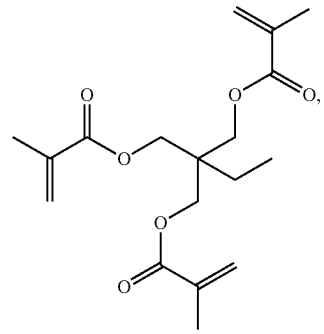

and a hydrophobic polymer; filters including the membranes, and methods of making and using the membranes, are disclosed.

14 Claims, No Drawings

ROBUST POLYMERIC MEMBRANE

BACKGROUND OF THE INVENTION

Polymeric membranes are used to filter a variety of fluids. However, there is a need for membranes that provide robust performance.

The present invention provides for ameliorating at least some of the disadvantages of the prior art. These and other advantages of the present invention will be apparent from the description as set forth below.

BRIEF SUMMARY OF THE INVENTION

An embodiment of the invention provides a hydrophilic porous membrane, comprising a random copolymer of:

(a) 2-hydroxyethyl methacrylate of formula (I):

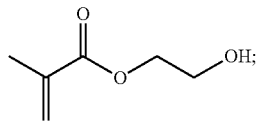

(b) an ethylene glycol dimethacrylate of formula (II):

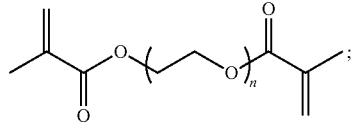

and (c) 1,1,1-trimethylolpropane trimethacrylate of formula (III):

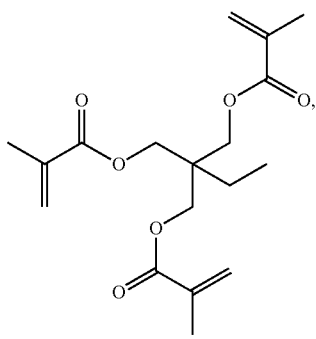 [SMILES: C=C(C)C(=O)OCC(CC)(COC(=O)C(=C)C)COC(=O)C(=C)C]

and, a hydrophobic polymer.

In accordance with another embodiment, a hydrophilic porous membrane is prepared by a process comprising polymerizing in a solvent:

(a) 2-hydroxyethyl methacrylate of formula (I):

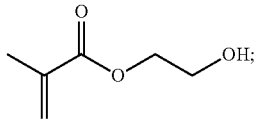

(b) an ethylene glycol dimethacrylate of formula (II):

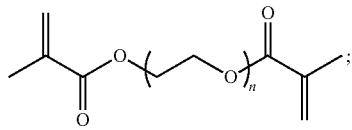

and (c) 1,1,1-trimethylolpropane trimethacrylate of formula (III):

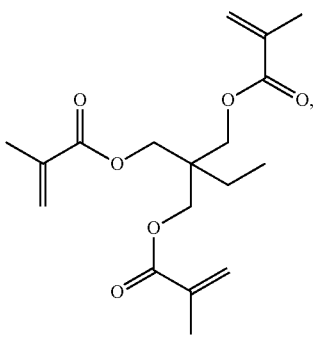 [SMILES: C=C(C)C(=O)OCC(CC)(COC(=O)C(=C)C)COC(=O)C(=C)C]

to form a random copolymer of (a), (b), and (c); wherein the solvent also includes at least one initiator and a hydrophobic polymer.

In accordance with other embodiments of the invention, filters and filter devices comprising the membranes, as well as methods of making and using the membranes, are provided.

DETAILED DESCRIPTION OF THE INVENTION

In accordance with an embodiment of the present invention, a hydrophilic porous membrane (preferably, a hydrophilic microporous membrane) is provided, the membrane comprising a random copolymer of:

(a) 2-hydroxyethyl methacrylate of formula (I):

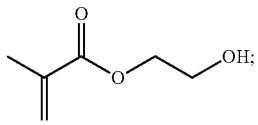

(b) an ethylene glycol dimethacrylate of formula (II):

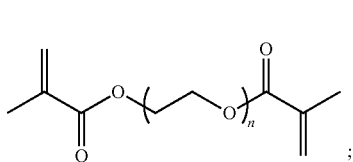

and (c) 1,1,1-trimethylolpropane trimethacrylate of formula (III):

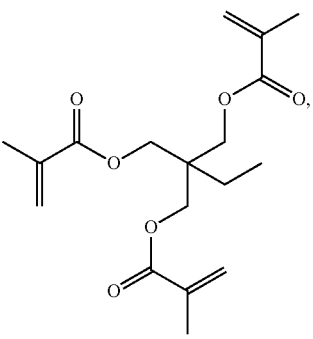 [SMILES: C=C(C)C(=O)OCC(CC)(COC(=O)C(=C)C)COC(=O)C(=C)C]

and, a hydrophobic polymer.

In accordance with another embodiment, a hydrophilic porous (preferably, microporous) membrane is prepared by a process comprising polymerizing in a solvent:

(a) 2-hydroxyethyl methacrylate of formula (I):

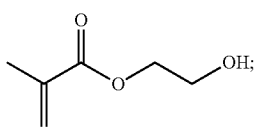

(b) an ethylene glycol dimethacrylate of formula (II):

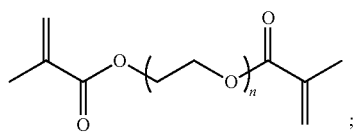

and (c) 1,1,1-trimethylolpropane trimethacrylate of formula (III):

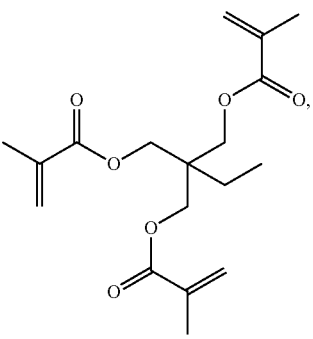 [SMILES: C=C(C)C(=O)OCC(CC)(COC(=O)C(=C)C)COC(=O)C(=C)C]

to form a random copolymer of (a), (b), and (c); wherein the solvent also includes at least one initiator and a hydrophobic polymer.

In other embodiments, filters and filter devices are provided, the filter and filter devices comprising at least one membrane.

A method of filtering fluid is also provided in accordance with another embodiment of the invention, the method comprising passing the fluid through at least one membrane, or a filter comprising at least one membrane, as described above. In one preferred embodiment, the fluid being filtered is a protein-containing fluid.

Advantageously, membranes according to the invention are highly hydrophilic, robust, and stable. They are suitable for providing high throughput. They include a hydrophilic acrylate polymer network prepared by polymerizing three or more different types of acrylate monomers, wherein one or more acrylates have three or more crosslinkable acrylate groups, and one or more acrylates are monoacrylate, wherein the acrylate polymer network is combined with at least one hydrophobic polymer having good mechanical properties. Without being bound to any particular theory, it is believed that the polymerization extent is maximized, stabilizing the polymeric network, resulting in high hydrophilicity, preferably about 82 dynes/cm (about $82 \times 10^{-5}$ N/cm), or more. The membranes are robust, such that they do not deteriorate after typical heat and/or Gamma radiation treatment. With respect to stability, the hydrophilicity of the membranes does not decrease after the membranes are soaked in strong acids (e.g., 1 M HCl), strong bases (e.g., 1 M NaOH), or organic solutions (e.g., ethanol or isopropyl alcohol) for extended periods of time, e.g., at least 48 hours. Stability in base solutions is particularly advantageous for applications involving the filtration of protein-containing solutions (e.g., pharmaceutical protein feed solutions), as base solutions are frequently used in removing protein types of foulants. Additionally, since the three dimensional network is very stable, the membrane extractable level is very low. The three dimensional network has a low protein and preservative binding capacity. Furthermore, the in-situ polymerization process for preparing the membranes is flexible, e.g., hydrophilic acrylate monomers, an initiator, and a hydrophobic polymer can be added into a solvent simultaneously, or the hydrophilic acrylate monomers and initiator can react with each other in a solvent before adding a hydrophobic polymer, or, for example, a hydrophobic polymer can be dissolved in solvent, followed adding the hydrophilic monomers and initiator to the solvent. The acrylate monomer polymerization can be conducted under vacuum, with nitrogen purging, or at atmospheric pressure.

One reaction system in accordance with an embodiment of the invention is shown below, wherein the solid curved line represents the bulk hydrophobic polymer chain.

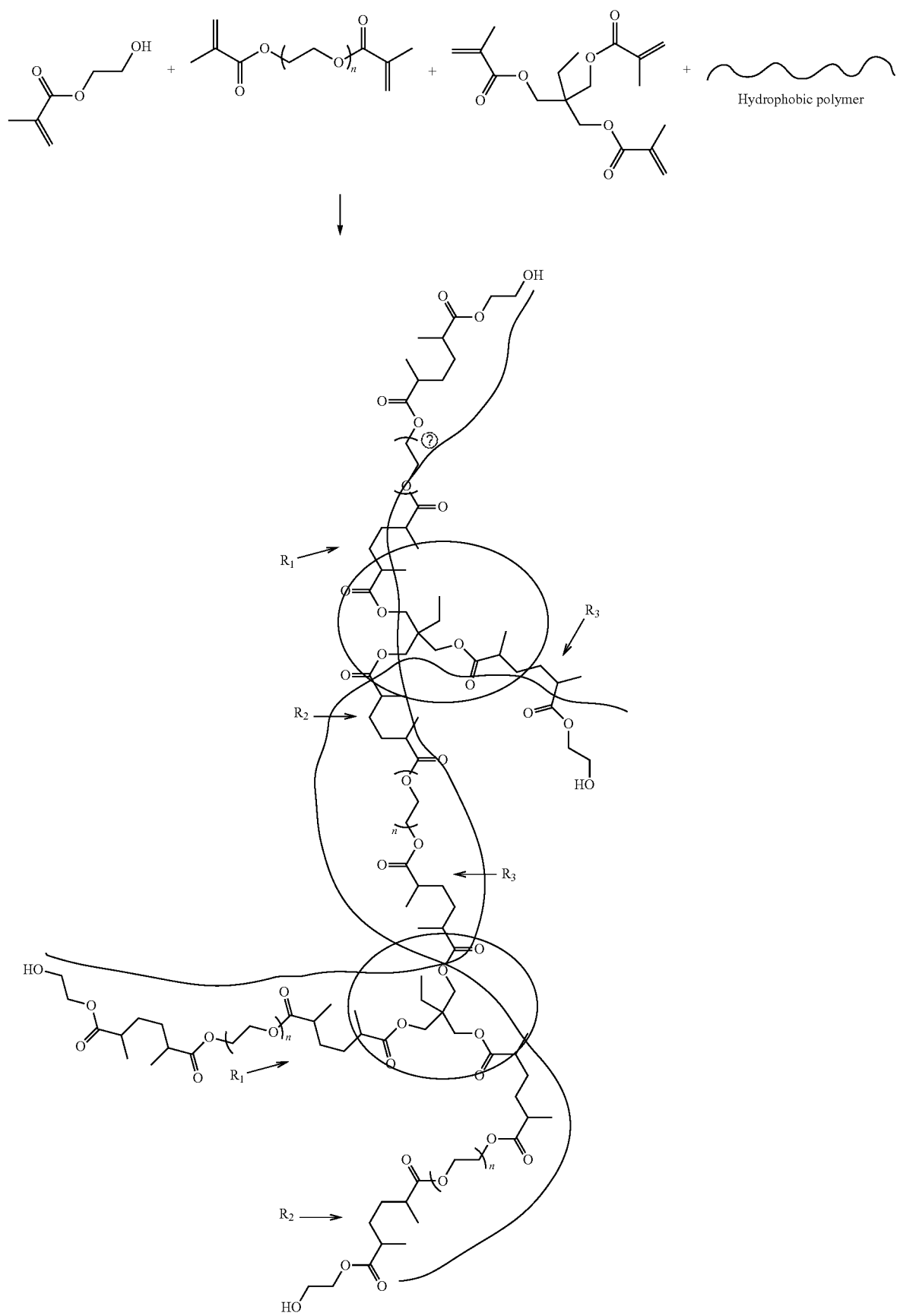

Each branch ($R_1$, $R_2$, $R_3$) results from random copolymerization of di-functional and mono-functional groups, e.g.,

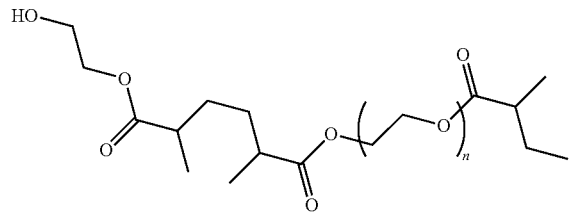

The branches ($R_1$, $R_2$, $R_3$) can connect to each other via random polymerization.

A variety of acrylates can be used in preparing membranes according to embodiments of the invention. Preferably, one or more of the three or more different types of acrylates have three or more crosslinkable acrylate groups, and one or more acrylates are monoacrylate. In one preferred embodiment, wherein three acrylates are used, hydroxyethyl methacrylate (HEMA; a neutral monofunctional monomer having no more than one functional group which undergoes polymerization) is used, along with poly(ethylene glycol) dimethacrylate (PEGDMA; a multifunctional acrylate having two functional groups) and trimethylolpropane trimethacrylate (TMPTMA; a multifunctional acrylate having three functional groups).

Embodiments of the invention are suitable for use with a variety of hydrophobic polymers, preferably, sulfones (e.g., polysulfones, including aromatic polysulfones such as, for example, polyethersulfone (PES), polyether ether sulfone (PEES), bisphenol A polysulfone, polyarylsulfone, polyphenylsulfone, and poly(phthalazinone ether sulfone ketone (PPESK)). As a result, the membranes have the desirable bulk properties of the hydrophobic polymers, with the desirable hydrophilic surface properties provided by the hydrophilic acrylate polymer network.

In accordance with an embodiment of the invention, a method of preparing a membrane comprises (a) casting a polymer solution comprising a polymeric network comprising a hydrophilic acrylate polymer network and a hydrophobic polymer onto a substrate; (b) carrying out phase inversion of the polymer solution to provide a membrane; and, optionally (c) washing and drying the membrane.

In a typical embodiment, the method comprises subjecting a reaction solution to conditions wherein one or more acrylates are cross-linked in-situ; obtaining a solution including the cross-linked acrylates, a hydrophobic polymer, and an initiator, and forming a polymer solution comprising a hydrophilic acrylate polymer network and the hydrophobic polymer, casting the polymer solution onto a substrate; carrying out phase inversion of the polymer solution to provide a membrane; and, optionally washing the membrane.

Typically, the phase inversion process for producing the membrane from the polymer solution involves casting or extruding a polymer solution into a thin film on the substrate, and precipitating the polymer(s) through one or more of the following: (a) evaporation of the solvent and nonsolvent, (b) exposure to a non-solvent vapor, such as water vapor, which absorbs on the exposed surface, (c) quenching in a non-solvent liquid (e.g., a phase immersion bath containing water, and/or another non-solvent or solvent), and (d) thermally quenching a hot film so that the solubility of the polymer is suddenly greatly reduced. Phase inversion can be induced by the wet process (immersion precipitation), vapor induced phase separation (VIPS), thermally induced phase separation (TIPS), quenching, dry-wet casting, and solvent evaporation (dry casting). Dry phase inversion differs from the wet or dry-wet procedure by the absence of immersion coagulation. In these techniques, an initially homogeneous polymer solution becomes thermodynamically unstable due to different external effects, and induces phase separation into a polymer lean phase and a polymer rich phase. The polymer rich phase forms the matrix of the membrane, and the polymer lean phase, having increased levels of solvents and non-solvents, forms pores.

A membrane-forming polymer solution is prepared by dissolving or dispersing monomer(s) and/or polymer(s) in a solvent or a mixture of solvents. A variety of polymer solutions are suitable for use in the invention, and are known in the art. Suitable polymer solutions can include, polymers such as, for example, sulfones (e.g., polysulfones, including aromatic polysulfones such as, for example, polyethersulfone (PES), polyether ether sulfone (PEES), polyether sulfone ketone (PESK), bisphenol A polysulfone, polyarylsulfone, and polyphenylsulfone, and poly(phthalazinone ether sulfone ketone (PPESK)). Polymer solutions can include a mixture of polymers, e.g., a hydrophobic polymer (e.g., a sulfone polymer) and a hydrophilic monomer and/or polymer (e.g., polyvinylpyrrolidone (PVP)).

In addition to one or more monomers and/or polymers, typical polymer solutions comprise at least one solvent, and may further comprise at least one non-solvent. Suitable solvents include, for example, dimethyl formamide (DMF); N,N-dimethylacetamide (DMAc); N-methyl pyrrolidone (NMP); dimethyl sulfoxide (DMSO), methyl sulfoxide, tetramethylurea; dioxane; diethyl succinate; chloroform; and tetrachloroethane; and mixtures thereof. Suitable nonsolvents include, for example, water; various polyethylene glycols (PEGs; e.g., PEG-200, PEG-300, PEG-400, PEG-1000); various polypropylene glycols; various alcohols, e.g., methanol, ethanol, isopropyl alcohol (IPA), amyl alcohols, hexanols, heptanols, and octanols; alkanes, such as hexane, propane, nitropropane, heptanes, and octane; and ketone, ethers and esters such as acetone, butyl ether, ethyl acetate, and amyl acetate; acids, such as acetic acid, citric acid, and lactic acid; and various salts, such as calcium chloride, magnesium chloride, and lithium chloride; and mixtures thereof.

Preferably, the solution comprising a polymer further comprises (typically, dissolved or dispersed in a solvent), for example, one or more polymerization initiators (e.g., any one or more of aliphatic azo compounds (e.g., 2,2'-azobis (2-amidinopropane)dihydrochloride (V50)), peroxides, ammonium persulfate, and combinations thereof), and/or minor ingredients such as surfactants and/or release agents.

Suitable components of solutions are known in the art. Illustrative solutions comprising polymers, and illustrative solvents and nonsolvents include those disclosed in, for example, U.S. Pat. Nos. 4,340,579; 4,629,563; 4,900,449; 4,964,990, 5,444,097; 5,846,422; 5,906,742; 5,928,774; 6,045,899; 6,146,747; and 7,208,200.

While a variety of polymeric membranes can be produced in accordance with the invention, in preferred embodiments, the membranes are sulfone membranes (more preferably, polyethersulfone membranes and/or polyarylsulfone membranes).

The membranes can be cast manually (e.g., poured, cast, or spread by hand onto the substrate) or automatically (e.g., poured or otherwise cast onto a moving belt having the substrate thereon).

A variety of casting techniques, including multiple casting techniques, are known in the art and are suitable. A variety of devices known in the art can be used for casting. Suitable devices include, for example, mechanical spreaders, that comprise spreading knives, doctor blades, or spray/pressurized systems. One example of a spreading device is an extrusion die or slot coater, comprising a casting chamber into which the casting formulation (solution comprising at least one polymer) can be introduced and forced out under pressure through a narrow slot. Illustratively, the solutions comprising polymers can be cast by means of a doctor blade with knife gaps in the range from about 100 micrometers to about 500 micrometers, more typically in the range from about 120 micrometers to about 400 micrometers.

A variety of casting speeds are suitable as is known in the art. Typically, the casting speed is at least about 3 feet per minute (fpm), more typically in the range of from about 3 to about 40 fpm, in some embodiments, at least about 5 fpm.

A variety of substrates are suitable for preparing membranes according to embodiments of the invention. For example, the substrate can be a non-paper substrate. Suitable substrates include, for example, glass, a polyester such as polyethylene terephthalate (PET) (e.g., commercially available as MYLAR); polypropylene; polyethylene (including polyethylene naphthalate (PEN); polyethylene terephthalate glycol (PETG)); polyimide; polyphenylene oxide; nylon; and acrylics.

The membranes can have any suitable pore structure, e.g., a pore size (for example, as evidenced by bubble point, or by $K_L$, as described in, for example, U.S. Pat. No. 4,340,479, or evidenced by capillary condensation flow porometry), a mean flow pore (MFP) size (e.g., when characterized using a porometer, for example, a Porvair Porometer (Porvair plc, Norfolk, UK), or a porometer available under the trademark POROLUX (Porometer.com; Belgium)), a pore rating, a pore diameter (e.g., when characterized using the modified OSU F2 test as described in, for example, U.S. Pat. No. 4,925,572), or removal rating media. The pore structure used depends on the size of the particles to be utilized, the composition of the fluid to be treated, and the desired effluent level of the treated fluid. Typically, membranes according to embodiments of the invention have pore size in the range of from about 0.01 to about 10 microns, preferably, in the range of from about 0.05 to about 5 microns.

The microporous surfaces of the membranes can have any suitable mean pore size, e.g., as determined by, for example, calculating the average surface pore size from an SEM at 500× or 20,000× magnification.

Typically, the thickness of membranes according to embodiments of the invention is in the range of about 0.5 mils (about 13 microns) to about 10 mils (about 254 microns), preferably, in the range of from about 3 mils (about 76 microns) to about 6 mils (about 153 microns).

The membrane can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869. Typically, the membrane has a CWST of greater than about 73 dynes/cm (about $73\times10^{-5}$ N/cm), and can have a CWST of about 78 dynes/cm (about $78\times10^{-5}$ N/cm) or more. In some embodiments, the membrane has a CWST of about 82 dynes/cm (about $82\times10^{-5}$ N/cm) or more, and in some preferred embodiments, a CWST of about 86 dynes/cm (about $86\times10^{-5}$ N/cm) or more.

The surface characteristics of the membrane can be modified (e.g., to affect the CWST, to include a surface charge, e.g., a positive or negative charge, and/or to alter the polarity or hydrophilicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van de Graff generator, ultraviolet light, electron beam, or to various other forms of radiation, or by surface etching or deposition using a plasma treatment.

A variety of fluids can be filtered in accordance with embodiments of the invention. Membranes according to embodiments of the invention, which are preferably microporous membranes, can be used in a variety of applications, including, for example, diagnostic applications (including, for example, sample preparation and/or diagnostic lateral flow devices), ink jet applications, filtering fluids for the pharmaceutical industry, filtering fluids for medical applications (including for home and/or for patient use, e.g., intravenous applications, also including, for example, filtering biological fluids such as blood (e.g., to remove leukocytes)), filtering fluids for the electronics industry (e.g., filtering photoresist fluids in the microelectronics industry), filtering fluids for the food and beverage industry, clarification, filtering antibody- and/or protein-containing fluids, filtering nucleic acid-containing fluids, cell detection (including in situ), cell harvesting, and/or filtering cell culture fluids. Alternatively, or additionally, membranes according to embodiments of the invention can be used to filter air and/or gas and/or can be used for venting applications (e.g., allowing air and/or gas, but not liquid, to pass therethrough). Membranes according to embodiments of the inventions can be used in a variety of devices, including surgical devices and products, such as, for example, ophthalmic surgical products.

In accordance with embodiments of the invention, the membrane can have a variety of configurations, including planar, pleated, hollow fiber and/or hollow cylindrical.

Membranes according to embodiments of the invention are typically disposed in a housing comprising at least one inlet and at least one outlet and defining at least one fluid flow path between the inlet and the outlet, wherein at least one inventive membrane or a filter including at least one inventive membrane is across the fluid flow path, to provide a filter device or filter module. In an embodiment, a filter device is provided comprising a housing comprising an inlet and a first outlet, and defining a first fluid flow path between the inlet and the first outlet; and at least one inventive membrane or a filter comprising at least one inventive membrane, the inventive membrane or filter comprising at least one inventive membrane being disposed in the housing across the first fluid flow path.

Preferably, for crossflow applications, at least one inventive membrane or filter comprising at least one inventive membrane is disposed in a housing comprising at least one inlet and at least two outlets and defining at least a first fluid flow path between the inlet and the first outlet, and a second fluid flow path between the inlet and the second outlet, wherein the inventive membrane or filter comprising at least one inventive membrane is across the first fluid flow path, to provide a filter device or filter module. In an illustrative embodiment, the filter device comprises a crossflow filter module, the housing comprising an inlet, a first outlet comprising a concentrate outlet, and a second outlet comprising a permeate outlet, and defining a first fluid flow path between the inlet and the first outlet, and a second fluid flow path between the inlet and the second outlet, wherein at least one inventive membrane or filter comprising at least one inventive membrane is disposed across the first fluid flow path.

The filter device or module may be sterilizable. Any housing of suitable shape and providing an inlet and one or more outlets may be employed.

The housing can be fabricated from any suitable rigid impervious material, including any impervious thermoplastic material, which is compatible with the fluid being processed. For example, the housing can be fabricated from a metal, such as stainless steel, or from a polymer, e.g., transparent or translucent polymer, such as an acrylic, polypropylene, polystyrene, or a polycarbonated resin.

The following examples further illustrate the invention but, of course, should not be construed as in any way limiting its scope.

Example 1

This example demonstrates the preparation of a membrane according to an embodiment of the invention.

A formulation is prepared having the following components and percentages: Polyethylene Glycol (PEG) (67.45%); Trimethylolpropane trimethacrylate (TMPTMA; Aldrich Chemical Co., Milwaukee, Wis.) (0.1%); Hydroxyethylmethacrylate (HEMA) (0.2%); PEG-400 dimethacrylate (PEGDMA) (0.6%); 2,2'-azobis(2-amidinopropane)dihydrochloride (V50; Wako Chemical, Richmond, Va.) (0.05%); DI water (2.0%); 58 kD molecular weight PES (BASF) (12.0%); NMP (11.0%); and DMF (6.6%).

The formulation is mixed at 47° C. for 24 hours, and degassed under vacuum for at least 12 hours prior to casting.

Using an extruder, membrane samples are cast on a stainless steel surface through an environmental chamber. The casting thickness is 200 micrometers. Casting is conducted at an air dew point of 20° C. and a stainless steel surface temperature of 26° C., wherein the residence time in the chamber is about 12 min. The membrane samples are leached with RO water for 10 min., followed by 40% Ethanol/60% RO water for 10 min., and 80° C. RO water for 10 min. The membrane samples are passed through an oven and dried at 65° C. for 10 min.

Example 2

This example demonstrates the properties of a membrane prepared as described in Example 1.

The membrane has the following properties: Thickness 3.40 mil (about 86.3 micrometers); $K_L$, 65.07 psi; water flow rate 33.04 mL·min$^{-1}$·cm$^{-2}$; normalized burst force (NBF) 1.52 lbs/mil; stretch 30.20%; CWST 86 dynes/cm ($86 \times 10^{-5}$ N/cm). The mean flow pore (MFP) size as determined by a POROLUX Porometer 1000 is about 0.35 microns.

Example 3

This example demonstrates the preparation of a membrane according to another embodiment of the invention.

A formulation is prepared having the following components and percentages: PEG (67.63%); TMPTMA (0.08%); HEMA (0.16%); PEGDMA (0.48%); V50 (0.05%); DI water (2.0%); high molecular weight (58 kD molecular weight) PES (BASF) (12.0%); NMP (6.6%); and DMF (11%).

The formulation is mixed at 47° C. for 24 hours, and degassed under vacuum for at least 12 hours prior to casting.

Membrane samples are cast, leached, and dried as described with respect to Example 1.

Example 4

This example demonstrates the properties of a membrane prepared as described in Example 3.

The membrane has the following properties: Thickness 2.90 mil (about 73.7 micrometers); $K_L$, 71.4 psi; water flow rate 31 mL·min$^{-1}$·cm$^{-2}$; NBF 1.30 lbs/mil; stretch 28.34%; CWST 85.78 dynes/cm ($85.78 \times 10^{-5}$ N/cm). The mean flow pore (MFP) size as determined by a POROLUX Porometer 1000 is about 0.32 microns.

Example 5

This example demonstrates the preparation of a membrane according to another embodiment of the invention.

A formulation is prepared having the following components and percentages: PEG (67.45%); TMPTMA (0.6%); HEMA (0.2%); PEGDM (0.1%); V50 (0.05%); DI water (2.0%); 58 kD molecular weight PES (12.0%); NMP (6.6%); and DMF (11%).

The formulation is mixed at 41° C. for 24 hours, and degassed under vacuum for 12 hours prior to casting.

Membrane samples are cast, leached, and dried, as described with respect to Example 1.

Example 6

This example demonstrates the properties of a membrane prepared as described in Example 5.

The membrane has the following properties: Thickness 3.84 mil (about 97.5 micrometers); $K_L$, 63.24 psi; water flow rate 29.08 mL·min$^{-1}$·cm$^{-2}$; NBF 0.902 lbs/mil; stretch 18.23%; CWST 85.78 dynes/cm ($85.78 \times 10^{-5}$ N/cm). The mean flow pore (MFP) size as determined by a POROLUX Porometer 1000 is about 0.38 microns.

Example 7

This example demonstrates the preparation of a membrane according to another embodiment of the invention.

A formulation is prepared having the following components and percentages: PEG (67.45%); TMPTMA (0.1%); HEMA (0.2%); PEGDMA (0.6%); V50 (0.05%); DI water (2.0%); 58 kD molecular weight PES (12.0%); NMP (11%); and DMF (6.6%).

The formulation is mixed at 47° C. under vacuum for 48 hours prior to casting.

Membrane samples are cast, leached, and dried, as described with respect to Example 1, except the drying is at 60° C. rather than 65° C.

Example 8

This example demonstrates the properties of a membrane prepared as described in Example 7.

The membrane hydrophilicity is measured by using various liquids having different surface tensions. The membranes are post treated by steam autoclaving at 125° C. for 1 hour, Gamma sterilized at 50 G/y, isopropyl alchohol (IPA) extracted for 3 hours, soaked in 1 M CH$_3$COOH at room temperature for 10 hours, soaked in 1 M HCl at room temperature for 10 hours, and soaked in 1 M NaOH at 60° C. for 10 hours. The membrane CWST remains stable at 86 dynes/cm ($86 \times 10^{-5}$ N/cm) even after the various post treatments.

Example 9

This example demonstrates the low level of extractables from a pleated membrane prepared as described in Example 7, compared to a pleated commercially available membrane, thus showing the increased robustness of a membrane according to an embodiment of the invention as compared to a commercially available membrane.

Pleated membranes are autocloaved and cut to provide samples from the pleat tips (outside pleats), middle location of pleats, and inside of the pleats (pleat valleys). The samples are soaked with boiling IPA for 3 hours to determine the distribution of extractables. Control samples that have not been autoclaved are also evaluated.

Without autoclaving, there is no significant difference in extractables between the outside, middle, and inside pleats, for both the commercially available and inventive membranes. However, the inventive membrane has a much lower level of IPA extractables (average 1.63%, about 36% lower) than the commercially available membrane (average 2.55%).

After autoclaving, the inventive membrane exhibits no significant difference in extractables between the outside, middle, and inside pleats. However, the commercially available membrane exhibits a much higher level of IPA extractables for the outside pleat as compared to the middle pleat (outside pleat level of extractables 3.35%, about 53% higher than the level for the middle, 2.20%) and the inside pleat (outside pleat level of extractables about 60% higher than the level for the inside, level 2.10%).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hydrophilic microporous membrane comprising a polymer blend comprising a hydrophobic polymer and a random copolymer of:
   (a) 2-hydroxyethyl methacrylate of formula (I):

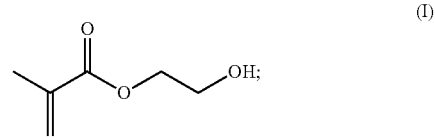

(b) polyethylene glycol-400 dimethacrylate; and
   (c) 1,1,1-trimethylolpropane trimethacrylate of formula (III):

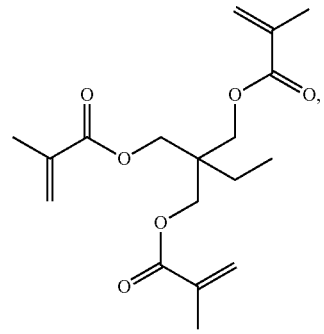 [SMILES: C=C(C)C(=O)OCC(CC)(COC(=O)C(=C)C)COC(=O)C(=C)C]

wherein the hydrophilic microporous membrane is prepared by casting a polymer solution comprising the polymer blend onto a substrate before carrying out phase inversion of the polymer solution to provide the hydrophilic microporous membrane.

2. A hydrophilic microporous membrane prepared by a process comprising polymerizing in a solvent:
   (a) 2-hydroxyethyl methacrylate of formula (I):

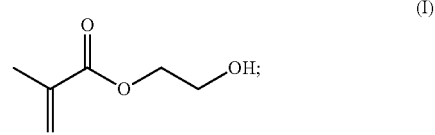

(b) polyethylene glycol-400 dimethacrylate; and
   (c) 1,1,1-trimethylolpropane trimethacrylate of formula (III):

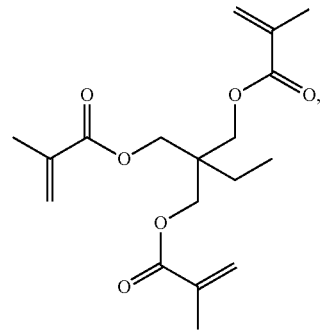 [SMILES: C=C(C)C(=O)OCC(CC)(COC(=O)C(=C)C)COC(=O)C(=C)C]

to form a random copolymer of (a), (b), and (c); wherein the solvent also includes (d) at least one initiator and (e) a hydrophobic polymer, before casting a solution comprising the random copolymer and the solvent onto a substrate, and carrying out phase inversion of the solution to provide the hydrophilic microporous membrane.

3. A hydrophilic microporous membrane prepared by a process comprising dissolving or dispersing in a solvent:

(a) 2-hydroxyethyl methacrylate of formula (I):

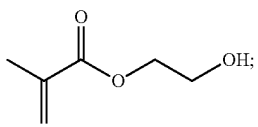

(b) polyethylene glycol-400 dimethacrylate;
(c) 1,1,1-trimethylolpropane trimethacrylate of formula (III):

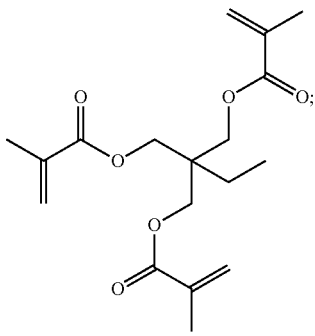 [SMILES: C=C(C)C(=O)OCC(CC)(COC(=O)C(=C)C)COC(=O)C(=C)C]

(d) a hydrophic polymer; and,
(e) at least one initiator;
wherein each of (a)-(e) is dissolved or dispersed in the solvent in any order, or simultaneously;
and,
polymerizing (a), (b), and (c) to form a random copolymer of (a), (b), and (c), before casting a solution comprising the random copolymer and the solvent onto a substrate, and carrying out phase inversion of the solution to provide the hydrophilic microporous membrane.

4. The hydrophilic membrane of claim 1, wherein the hydrophobic polymer is a sulfone polymer.

5. A method of filtering a fluid, the method comprising passing the fluid through the membrane of claim 1.

6. The method of claim 5, wherein the fluid is a protein-containing fluid.

7. The hydrophilic membrane of claim 2, wherein the hydrophobic polymer is a sulfone polymer.

8. The hydrophilic membrane of claim 3, wherein the hydrophobic polymer is a sulfone polymer.

9. A method of filtering a fluid, the method comprising passing the fluid through the membrane of claim 2.

10. A method of filtering a fluid, the method comprising passing the fluid through the membrane of claim 3.

11. A method of filtering a fluid, the method comprising passing the fluid through the membrane of claim 4.

12. The method of claim 9, wherein the fluid is a protein-containing fluid.

13. The method of claim 10, wherein the fluid is a protein-containing fluid.

14. The method of claim 11, wherein the fluid is a protein-containing fluid.

* * * * *